United States Patent [19]

Takeda et al.

[11] 4,377,001

[45] Mar. 15, 1983

[54] METHOD FOR OPTICAL DETERMINATION OF SATURATION TEMPERATURE AND APPARATUS THEREFOR

[75] Inventors: Reiji Takeda; Shozo Oikawa, both of Obihiro, Japan

[73] Assignee: Nippon Tensaiseito Kabushiki Kaisha, Tokyo, Japan

[21] Appl. No.: 234,470

[22] Filed: Feb. 17, 1981

[30] Foreign Application Priority Data

Oct. 29, 1979 [JP] Japan .......................... 54-148784[U]
Feb. 18, 1980 [JP] Japan ................................. 55-17819

[51] Int. Cl.$^3$ ...................... G01N 25/12; G01N 21/51
[52] U.S. Cl. ......................................... 374/17; 356/38
[58] Field of Search ................. 73/61 R, 61.1 R, 61.2, 73/61.3, 17; 356/36, 38, 246, 440; 350/63

[56] References Cited

U.S. PATENT DOCUMENTS 2,716,371  8/1955  Still ...................................... 73/61.3
4,240,691 12/1980  Holmquist et al. ................... 350/63

OTHER PUBLICATIONS

"The Determination of the Saturation Temperature of Sugar Syrups by a Photometric Method", by P. G. Wright, The International Sugar Journal, Jan. to Dec. 1978, vol. LXXX, pp. 40-44.

*Primary Examiner*—S. Clement Swisher
*Attorney, Agent, or Firm*—Stevens, Davis, Miller & Mosher

[57] ABSTRACT

A method and apparatus for determining the saturation temperature of a given substance dissolved in a solution under test, based on the principle that the change in the temperature of the solution causes a specific change in the amount of light being passed through the solution. The accuracy of the determination of saturation temperature is augmented by passing a preheated air through an empty space formed between the test cell and the air seal glass thereby precluding otherwise possible formation of dew-condensation on the air seal glass. This invention is characterized by forming a thin layer of fine crystals of the substance deposited fast on the bottom face of the test cell and pouring the solution onto the thin layer in the test cell.

6 Claims, 9 Drawing Figures

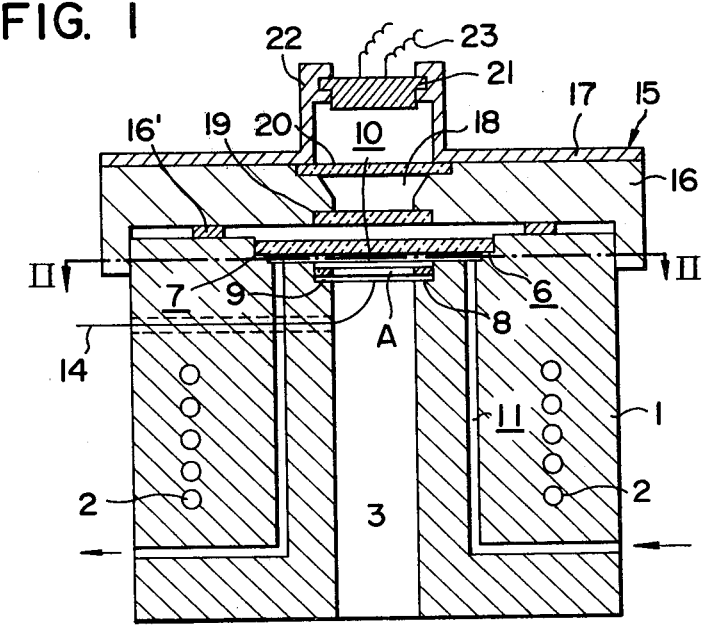
FIG. 1
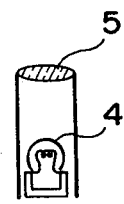
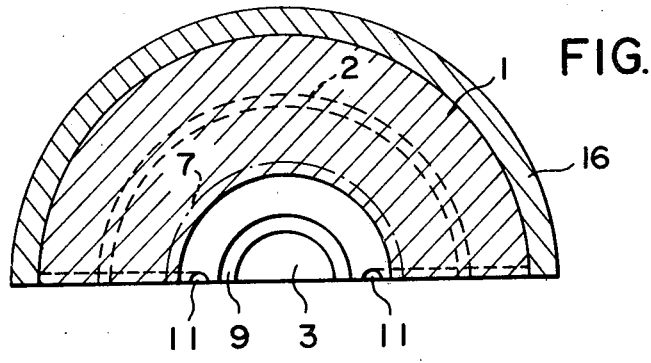
FIG. 2

FIG. 4 PRIOR ART
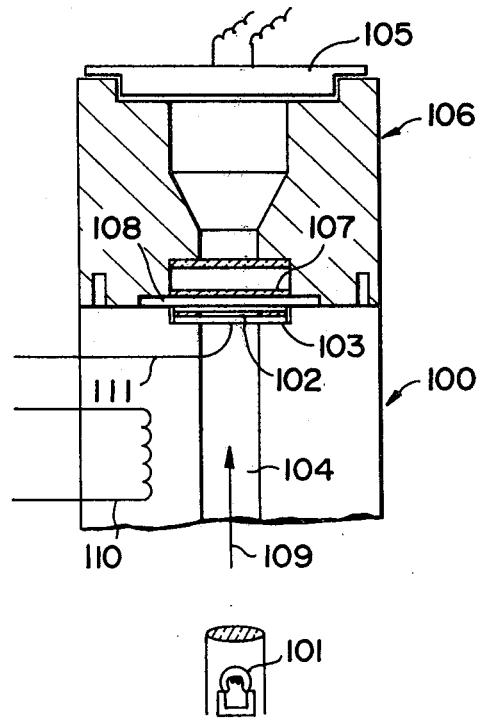
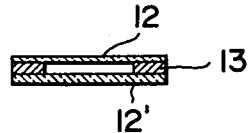
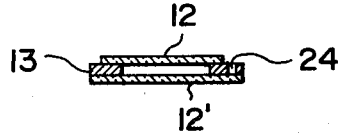
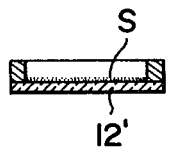
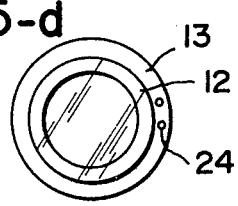

METHOD FOR OPTICAL DETERMINATION OF SATURATION TEMPERATURE AND APPARATUS THEREFOR

BACKGROUND OF THE INVENTION

This invention relates to an improved method and apparatus for optical determination of the saturation temperature of a solution which dissolves a solute.

The saturation temperature meter is an instrument which is necessary when, in organic and inorganic chemical industries and food industry, the saturation temperatures of varying substances are to be determined for the purpose of scientific management of crystals during the eduction of crystals in solutions. No measure established for providing effective determination of saturation temperature has been known to date.

Recently, an improved saturation temperature meter designed for optical determination of saturation temperature has been reported in the International Sugar Journal, Vol. LXXX, 1978, pp 40–43 (published at 23a Easton Street, High Wycombe Bucks, England).

As illustrated in FIG. 4, this temperature meter is composed mainly of a light source 101, a heating unit 100 provided with a light path 104 and a mount 103 for a test cell 102, and a light-receiving unit 106 provided with a light-receiving element 105. The temperature meter is prepared for operation by placing a solution subjected to test in the test cell 102, causing fine crystals of the solute dissolved in the solution to be added to and suspended in the solution to obtain a test specimen, mounting the test cell 102 containing the test specimen on the cell mount 103 and placing the heating unit 100 on top of the light-receiving unit 106. At this point, an empty space 108 occurs between a heat retaining glass 107 disposed in the lower portion of the light-receiving unit 106 and the test cell 102. With the meter so prepared, admission of a light 109 via the light path 104 upwardly from the lower end of the test cell 102 is started and a heater 110 is switched on to effect gradual indirect heating of the test specimen in the test cell 102. As the heating is continued, the temperature of the test specimen increases and eventually reaches a point at which the fine crystals in the test specimen are dissolved. At this point, a change occurs in the light penetrating through the test cell 102 (the amount of light allowed to penetrate through the cell increases because the scattering of light is decreased on dissolution of fine crystals) and, consequently, a heavy change occurs in the amount of light being continuously received by the light-receiving (photoelectric) element 105. This change manifests itself in a change in the amount of electricity being generated in the light-electricity conversion in the light-receiving element 105. In the meantime, the temperature of the test specimen is continuously measured by a temperature measuring unit 111 which is held in contact with the lower surface of the test cell 102. This temperature meter, therefore, tells the saturation temperature of the solution under test by the combination of the point of the aforementioned change in the amount of electricity and the temperature of the test specimen existing at that point.

In the conventional saturated temperature meter such as described above, during the elevation of the temperature of the test specimen, the test specimen in the test cell 102 and the gas in the empty space 108 gain in volume because of the phenomenon of thermal expansion. Consequently, an increased portion of the gas and a small volume of steam issuing from the surface of the test specimen leak into and fill out the empty space 108, giving rise to a state of steam saturation. In this case, the relation between the temperature of the test cell 102 ($T_1$) and that of the heat retaining glass 107 ($T_2$) is $T_1 > T_2$ under normal working conditions. Consequently, part of the steam filling up the empty space 108 comes into contact with the surface of the heat retaining glass 107 and forms dew-condensation thereon. The present inventors' experience tells that where the temperature ($T_2$) is in the range of from 5° to 10° C., the dew-condensation occurs when the temperature difference ($T_1-T_2$) is about 0.2° C., and that even where the temperature ($T_2$) falls within the range of from 25° to 30° C., the dew-condensation formation ensues when the temperature difference ($T_1-T_2$) is about 1° C. When the dew-condensation forms as described above, it causes scattering of the light penetrating through the test cell 102 to impair the accuracy of the determination. If the heating speed is to be lowered enough to preclude the dew-condensation formation, the speed must be brought down to an extreme lever such that the determination requires an excessively long time, the change in the volume of the penetrating light occurs very slowly and the saturation point appears very vaguely.

Further according to the conventional saturation temperature meter, the test specimen is prepared by suspending added fine crystals of the solute in the solution under test. In case where the solution under test has a high purity or where the solution involves a high degree of supersaturation, therefore, the initial crystallization (occurrence of pseudocrystals) either during or after the preparation of the test specimen proceeds very quickly so that the procedure of determination demands high skill or the reproducibility of the determined values is impaired.

SUMMARY OF THE INVENTION

This invention has been made with a view to mending the various disadvantages suffered by the conventional saturation temperature determination as described above.

An object of this invention is to provide a method for the determination of saturation temperature which precludes external disturbance of the results of determination and permits a reduction in the time required for the determination.

Another object of this invention is to provide a test specimen which enjoys stability during and after the preparation thereof.

Yet another object of this invention is to provide an improved apparatus for accomplishing the objects described above.

The present invention provides easy determination of the saturation temperature even in the case of solutions which behave unstably at high degrees of purity or supersaturation and which, accordingly, have heretofore been either barely practicable with very deliberate, skillful techniques or absolutely impracticable with any techniques. Thus, it can be advantageously utilized for the routine control of crystallization operations involved such as in the chemical and food industries.

BRIEF DESCRIPTION OF THE DRAWINGS

The objects of this invention and the advantages thereof will be fully comprehended from the accompanying drawing to be described below.

FIG. 1 is a sectioned side view illustrating, in general outline, the apparatus for the determination of saturation temperature according to this invention.

FIG. 2 is a cross section as viewed along the line II—II indicated in the diagram of FIG. 1.

FIG. 4 is a sectioned side view illlustrating, in general outline, the conventional apparatus for determination of the saturation temperature.

FIG. 5-a is a sectioned side view of a typical test cell.
FIG. 5-b is a sectioned side view illustrating the condition in which fine crystals are deposited fast on the cell.
FIG. 5-c is a sectioned side view of a typical test cell of improved design. FIG. 5-d is a front view of the test cell of FIG. 5-c.

DETAILED DESCRIPTION OF THE INVENTION

Figure 3:
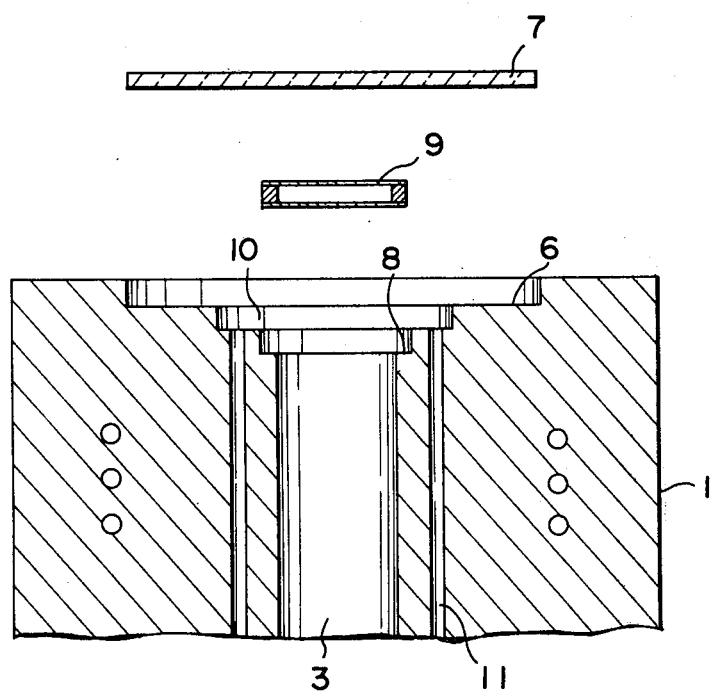
FIG. 3 is a partial sectioned side view for illustrating the steps for carrying a test cell and an air seal glass.

In the drawing, 1 denotes a warmer which is generally constructed in a cylindrical form with a metal such as cast aluminum which excels in thermal conductivity. Inside the warmer 1, a heat generator 2 is buried and used for elevating the temperature of the warmer 1 to a desired level. The heat generator 2 is something like an electric heating coil capable of being adjusted to a desired temperature. The warmer 1, at the center thereof, contains a cylindrical opening in the vertical direction to form an irradiating light path 3. The light path 3 is so disposed that the light from a light source 4 positioned under the light path 3 is collected by a lens 5 and passed upwardly through the light path 3. Inside the warmer 1 in the upper part of the irradiating light path 3, a mounting base 6 is formed for supporting in position an air seal glass 7 concentrically relative to the light path 3. This base 6, which serves as a mounting base for the air seal glass, has a diameter greater than the diameter of the irradiating light path 3. The mounting base 6 supports the air seal glass 7 in a direction perpendicular relative to the light path 3. At a prescribed distance below the mounting base 6 for the air seal glass 7, a mounting base 8 for supporting a test cell 9 is concentrically formed relative to the mounting base 6. This base 8, which serves as a mounting base for the test cell 9, maintains the test cell 9 parallel to the air seal glass 7. The distance between the mounting base 6 for the air seal glass 7 and the mounting base 8 for the test cell 9 is so fixed that, when the test cell 9 and the air seal glass 7 are set fast in position on the respective bases 6, 8, an empty space 10 within the range of from 0.5 mm to several mm is formed between the cell 9 and the glass 7. This is a substantially closed space which is enclosed with the air seal glass 7, the test cell 9 and the inner wall of the warmer 1. With this space 10, air ducts 11 pierced through the warmer 1 are allowed to communicate respectively at one end thereof, to permit flow of air through the air ducts and the space in the direction of the arrow. The test cell 9, therefore, is heated on the both sides, i.e., on the lower side by the heat received directly from the warmer 1 and on the upper side by the heat from the air which has been heated by the warmer 1. The test cell 9 is generally formed by inserting a washer 13 made of a corrosionproof, highly thermoconductive metal such as, for example, brass between two circular glass plates 12, 12' disposed as illustrated in FIG. 5-a. The lower glass plate 12' is joined fast to the washer 13, and the upper glass plate 12 is separably mounted on the washer 13. Thus, the test cell 9 contains an empty space for admitting a test specimen between the opposed glass plates 12, 12'. A temperature-measuring terminal 14 is disposed in a position such that it will come into contact with the lower glass plate 12' when the test cell 9 is mounted in position on the mounting base 8 for the test cell 9. Generally, a precision grade thermocouple is used as the temperature-measuring terminal 14. Instead of using a construction incorporating a washer as described above, the test cell may be formed by simply combining two transparent glasses.

Denoted by 15 is a light-receiving unit, which is freely removably mounted on top of the warmer 1. The light-receiving unit 15 is desired to be composed of two components of different materials; a base 16 made of a heat-resistant synthetic resin of a low thermal conductivity and adapted to come into direct contact with the warmer 1 and a member 17 disposed on the base 16 and adapted to support in position a light receiving element 21. For the purpose of ensuring thorough release of the heat transmitted from the base 16 and preventing the light receiving element 21 from possible temperature elevation, the member 17 is desired to be made of a material of high thermal conductivity. Copper is an ideal example of the material for the member 17. By 16' are denoted legs projecting from the lower side of the base 16. These legs 16' serve to form an empty space between the warmer 1 and the base 16 and, thereby, permitting adiabatic effect insulation. Denoted by 18 is a light path leading to the light-receiving unit and is formed coaxially with the irradiating light path 3. A heat retaining glass 19 is disposed below the light path 18 for the light-receiving unit 15. Accordingly, the light which has passed through the heat retaining glass 19 is forwarded through a polarizing lens 20 to the light-receiving element 21. The light-receiving element 21 is formed of a photosensitive material such as a photodiode. To support this element 21 in position, a rising portion 22 is formed at the central upper portion of the member 17. Held in a fixed position at all times, the light-receiving element 21 is allowed to detect the amount of light received via the light-receiving path 18. The light which impinges upon this light-receiving element 21 is converted into electricity. An output terminal 23 is connected to the light-receiving element 21. This terminal is extended and connected to a recorder or measuring instrument which is not illustrated.

The apparatus of the present invention is constructed as described above. Now, the operation of this apparatus for the determination of saturation temperature will be described below.

The apparatus is prepared for the operation by first suspending in a solvent fine crystals of a solute dissolved in a solution subjected to test pouring the resultant suspension dropwise to the light-penetrating bottom face of the test cell 9, subsequently vaporizing the solvent by suitable means such as application of heat, thereby causing the fine crystals of the solute to be deposited fast in the form of a thin layer S on the light-penetrating face as illustrated in FIG. 5-b.

The solvent used in this case should avoid causing an alteration such as dissolution or reaction on the solute and possess an appropriate velocity of vaporization. A solvent satisfying this requirement may be suitably selected by taking into due consideration physical properties and chemical properties possessed thereby. In case where sucrose is used as a solute, for example, acetone proves to be a suitable solvent and brings about fast deposition of the solute satisfactorily. In this case, ether possesses a too high vaporization velocity and alcohol inversely possesses a too low vaporization velocity to bring about desired fast deposition of the solute. Optionally, a mixture of two or more solvents, each fulfilling the requirement for avoiding an undesirable alteration of the solute, may be used.

Into the test cell 9 in which the fine crystals have been deposited fast in the form of a thin layer S as described above, the solution under test is slowly poured to cover the upper glass plate 12, completing the preparation of a test specimen.

Figure 6:
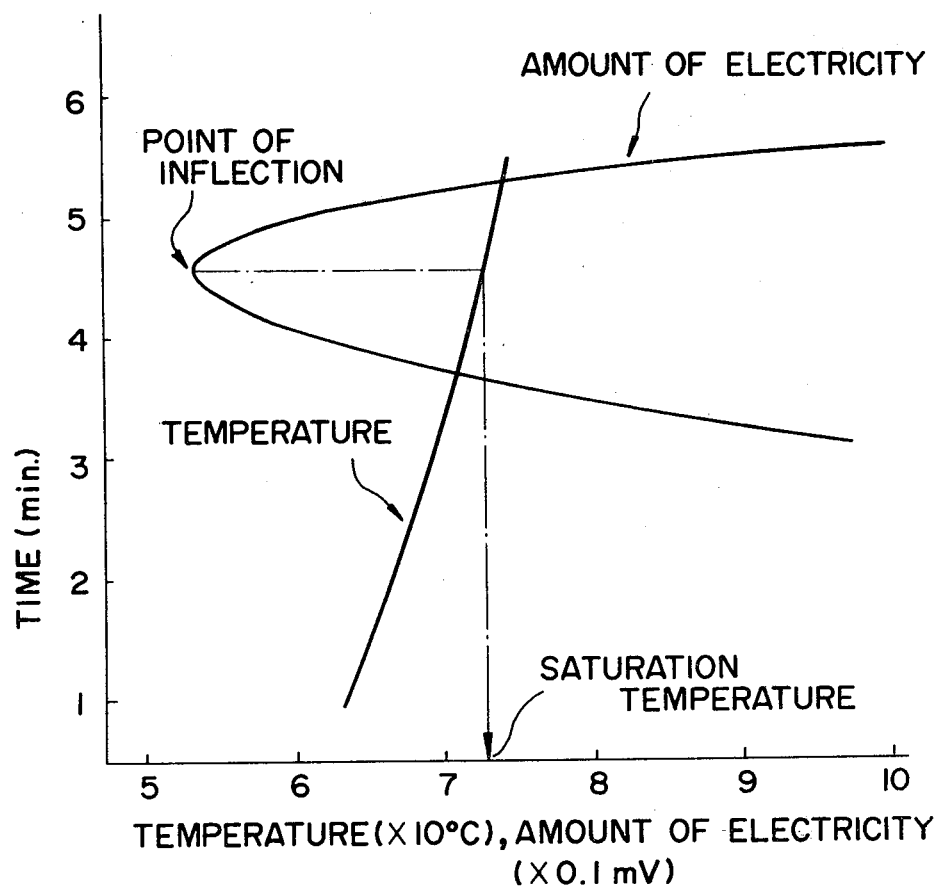
FIG. 6 is a diagram of the characteristic curve representing the relation of temperature amount of electricity and time.

The test cell 9 containing the test specimen as described above is set in position on the mounting base 8 illustrated in FIG. 1. Above the test cell 9, the air seal glass 7 is set in position on the mounting base 6. Preparation of the apparatus for the determination is then completed by mounting the light-receiving unit 15 on the warmer 1. Then, the current of air is sent through the air duct 11 and the flow of electricity is advanced to the heat generator 2 and the light source 4 is switched on to forward the light to the cell 9 containing the test specimen. After 100 parts of the light has entered the test specimen layer A, some part of the light is absorbed by the solution and some part thereof is randomly scattered by very fine crystals forming the thin layer S. Consequently, less than 100 parts of the light penetrates through the cell 9 and reaches the light-receiving element 21, there to be converted into a corresponding amount of electricity. In proportion as the temperature of the test specimen increases, the amount of the light absorbed by the solution increases, that of the light allowed to reach the light-receiving element 21 decreases and the amount of electricity generated in consequence of the conversion decreases. The curve plotting the amount of electricity recorded continuously along the course of time indicates that the amount of electricity decreases with the lapse of time (FIG. 6).

As the heating further proceeds to a point where the fine crystals forming the thin layer S begin to dissolve, i.e., where the saturation temperature is just passed, the scattering of the light begins to decrease owing to the decrease in the amount of the fine crystals and the amount of the light reaching the light-receiving element 21 suddenly changes toward an increasing trend. Consequently, a point of sharp inflection appears in the curve plotting the continuous change of the amount of electricity generated. The temperature which corresponds to this point of sudden inflection in the amount of electricity is the saturation temperature of the solution under test. By combining the aforementioned amount of electricity and the temperature of the test specimen indicated on the temperature-measuring terminal 14, therefore, the saturation temperature can be readily determined, as in FIG. 6.

The method for the determination of the saturation temperature according to the present invention has been described. The test specimen to be used for the determination is prepared without entailing the step of causing fine crystals of the solute to be suspended in the solution under test as practiced conventionally. Thus, the occurrence of pseudo-crystals during or after the preparation of the test specimen is precluded and, consequently, the determination is allowed to afford accurate results.

Further in the case of this invention, the air which has been warmed by the warmer 1 is blown in the empty space 10 formed on the test cell 9. The surface temperature of the air seal glass 7 defining the upper boundary of the empty space 10, therefore, is substantially equal to the temperature of the test cell 9, and the steam leaking from the cell 9 because of thermal expansion is not suffered to form dew-condensation in the empty space 10 as experienced with the conventional apparatus. Since the leaking steam is constantly purged out of the empty space 10 by the current of air flowing through the air duct 11, no steam is suffered to stagnate anywhere within the empty space 10.

The improvements offered by this invention serve to expedite the determination and, at the same time, greatly enhance the reproducibility of the results of determination.

For the purpose of comparison, the method and apparatus of the present invention and those of the conventional technique were used to determine the saturation temperature of a sucrose solution. The results were as shown in Table 1. Comparison of the accuracy of determination expressed in terms of dispersions in the measured values reveals that the dispersions in the results obtained by this invention were small and the average values satisfactorily agreed to the theoretical values.

The procedure of the determination and the results of the determination (Table 1) are explained below. In the case of this invention, the procedure followed in the preparation of the apparatus for determination comprised suspending in acetone a small amount of sucrose crystals pulverized in advance to a particle size of not more than 200 mesh, pouring the resultant suspension dropwise little by little onto the light-penetrating bottom surface (glass plate 12') of the test cell 9 mounted on a hot plate heated to 80° to 100° C., allowing the fine crystals to form an apparently uniform thin layer, vaporizing acetone thereby causing the thin layer of fine crystals to be fast deposited on the glass plate and, on completion of the fast deposition of the fine crystals, allowing the test cell 9 to cool off, gently pouring into the test cell 9 a sucrose solution having a purity of 99% and a total solids content of 75% (w/w), and covering the test cell 9 with a lid (glass plate 12'). Then, by following the procedure described above, the determination of the saturation temperature was carried out by heating the test specimen at a temperature increase rate of 5° C./minute. In the case of the conventional technique, a test specimen was prepared by gently stirring about 5 g of a sucrose solution having the same purity and concentration as mentioned above with 1 to 2%, based on the sucrose solution, of a more or less wet powder sucrose obtained by centrifuging sucrose crystals of a particle size of not more than 200 mesh in an alcohol, thereby causing the sucrose crystals to be suspended in the sucrose solution. This test specimen was poured in the test cell 9 and subjected to the determination of saturation temperature.

TABLE 1

| Method | Item | | | | | Average | Dispersion |
|---|---|---|---|---|---|---|---|
| | 1 | 2 | 3 | 4 | 5 | | |
| This | | | | | | | |

TABLE 1-continued

| Method | Item 1 | 2 | 3 | 4 | 5 | Average | Dispersion |
|---|---|---|---|---|---|---|---|
| invention | 63.1 | 63.9 | 64.2 | 63.4 | 63.6 | 63.64° C. | ±0.38° C. |
| Conventional technique | 60.2 | 63.2 | 62.0 | 58.5 | 61.3 | 61.04° C. | ±1.6° C. |

For the sucrose solution to be tested which has a concentration of 75%, the theoretical value of the saturation temperature is 64° C. (as reported by Herzfeld).

The present invention is typically worked as described above. It admits of various modifications within the purview of the spirit of the invention and should not be limited strictly to the foregoing description.

As a simple measure for effecting fast deposition of a thin layer S of fine crystals of the solute on the light-penetrating bottom surface of the test cell 9, the aforementioned technique resorting to the vaporization of the solvent may be substituted by a technique of fastening an adhesive tape to the light-penetrating bottom surface and allowing the fine crystals of the solute to be laid fast in a small thickness on the viscous inner side of the adhesive tape or a technique of applying a non-drying paste to the light-penetrating bottom surface and similarly causing the fine crystals to be laid fast on the layer of the paste, for example. Although the technique making use of the adhesive tape involves a slightly greater dispersion of the found values than the technique resorting to the vaporization of the solvent or the technique utilizing the application of the non-drying paste, the increase of the dispersion is not so heavy as to pose any problem from the practical point of view. The technique using the non-drying paste affords results of determination favorably comparable with those obtained by the technique resorting to the vaporization of the solvent when the selection of the paste is proper. In the experiment on the technique resorting to the vaporization of the solvent described above, acetone was used as the solvent. This does not mean that acetone is the sole choice as the solvent. Depending on the nature of the solute in use, other suitable solvent may be selected by taking into account the temperature of heating of the test cell 9 and the velocity of vaporization of the solvent.

Optionally, the device for passing the preheated air through the air duct 11 may be suitably substituted by a device which is adapted to preheat the air with a separate unit, a device which directly feeds the air preheated with an external, adjustable heat source to the empty space 10 and discharges the spent air from the empty space 10 or any other device which fulfils the essential requirement that the air with an adjusted temperature should be delivered to and discharged from the empty space 10 at a fixed flow rate. The ease with which the test cell 9 is inserted into and removed from the apparatus may be enhanced by giving a smaller diameter to the upper glass 12 than to the lower glass 12' as illustrated in FIG. 5-c and boring a small pickup hole 24 at an exposed portion of the upper surface of the washer 13.

The following working examples are to illustrate typical embodiments of this invention.

EXAMPLE 1

A test cell 9 was set at rest on a hot plate 90° C. in temperature. A suspension prepared by suspending a sucrose powder of a particle size of 200-mesh-through in a concentration of about 1% in acetone was added dropwise to the test cell 9 and was vaporized to form a very thin, uniform layer S deposited fast to the test cell 9. After the test cell 9 was cooled, a varying test specimen indicated below was poured into the test cell 9. The test cell 9 was mounted on a mounting base 8 in an apparatus constructed as shown in FIG. 1 for the determination of saturation temperature. The apparatus was operated by feeding the preheated air to the empty space 10 thereby elevating the temperature of the test specimen at a temperature increasing rate of 3° C./minute. The test specimen was prepared by allowing the molasses produced at Memuro Plant of Nippon Tensaiseito Kabushiki Kaisha to stand in a refrigerator at 5° C. for 60 days, adding sucrose to the cooled molasses and keeping the resultant mixture stirred in a constant temperature bath (controlled accurately to within 0.5° C.) for 72 hours thereby saturating the mixture with an excess crystalline sugar.

| | |
|---|---|
| Test specimen A | Bath temperature 60° C., true sucrose purity 56% |
| Test specimen B | Bath temperature 70° C., true sucrose purity 60% |

| | Test results (in °C.) | | | | | |
|---|---|---|---|---|---|---|
| Item | 1 | 2 | 3 | 4 | 5 | Average |
| Test specimen A | 61.2 | 60.5 | 60.3 | 61.6 | 60.3 | 60.8 ± 0.53 |
| Test specimen B | 69.8 | 69.0 | 69.0 | 69.3 | 70.1 | 69.4 ± 0.41 |

EXAMPLE 2

A double-faced adhesive tape made be Nichiban K.K. was applied to cover accurately the inner bottom surface of the test cell 9. A sucrose powder having a particle size of 200-mesh-through was placed on the adhesive tape in the test cell 9 and was blown with air to expel loose sucrose particles and leave behind a very thin layer S of fine crystals deposited fast on the test cell 9. The same test specimen as used in Example 1 was poured in the test cell 9, which was subjected to the test by following the procedure of Example 1, with the temperature increasing rate fixed at 3° C./minute.

| | Test results (in °C.) | | | | | |
|---|---|---|---|---|---|---|
| Item | 1 | 2 | 3 | 4 | 5 | Average |
| Test specimen A | 61.8 | 61.0 | 60.9 | 59.8 | 62.6 | 61.2 ± 1.1 |
| Test specimen B | 71.2 | 72.1 | 69.8 | 72.0 | 70.8 | 71.8 ± 0.95 |

EXAMPLE 3

A non-drying paste produced by Nogawa Chemical K.K. and marketed under the trademark designation of "Diabond 605#" was applied in a thin layer to the inner bottom of the test cell 9. A sucrose powder having a particle size of 200-mesh-through was placed on the non-drying paste in the test cell 9 and was blown with air to expel loose sucrose particles and leave behind a very thin layer S of fine crystals deposited fast on the test cell 9, which was subjected to the test by following the procedure of Example 1, with the temperature increasing rate fixed at 3° C./minute.

| | Test results (in °C.) | | | | | |
|---|---|---|---|---|---|---|
| Item | 1 | 2 | 3 | 4 | 5 | Average |
| Test specimen A | 60.2 | 59.4 | 61.1 | 60.5 | 60.7 | 60.4 ± 0.57 |

-continued

| | Test results (in °C.) | | | | | |
|---|---|---|---|---|---|---|
| Item | 1 | 2 | 3 | 4 | 5 | Average |
| Test specimen B | 70.1 | 69.5 | 69.0 | 69.8 | 70.5 | 69.8 ± 0.51 |

What is claimed is:

1. A method for the optical determination of the saturation temperature of a given substance in a solution subject to test by a procedure involving the steps of placing the solution in a test cell, suspending therein fine crystals of the solute dissolved in the solution thereby preparing a test specimen, mounting the test cell now containing the test specimen on a mounting base formed in a temperature-adjustable heater, gradually elevating the temperature of the test specimen and throwing a light upwardly at the test specimen, receiving the light penetrating through the test specimen on a photoelectric element and calculating the saturation temperature based on the temperature of the heat specimen and the amount of electricity generated in the photoelectric element, which method is characterized by causing the fine crystals of the solute to be deposited fast in the form of a thin layer on the light-penetrating surface of the test cell and then, pouring said solution on the deposited thin layer to prepare a test specimen, mounting the test cell containing the test specimen on said mounting base, gradually elevating the temperature of the test specimen and throwing light upwardly at the test specimen, at that time an empty space on the cell is made as a closed empty space and a preheated air is passed through the closed empty space.

2. The method according to claim 1, wherein said fast deposition of said fine crystals in a thin layer is accomplished by suspending the fine crystals of the solute in the solvent, dropping the suspension onto the light-penetrating face of the test cell and subsequently vaporizing the solvent.

3. The method according to claim 1, wherein said fast deposition of said fine crystals is effected by fastening an adhesive tape to the light-penetrating face of the test cell and causing the fine crystals to be fast deposited on the adhesive tape.

4. The method according to claim 1, wherein said fast deposition of said fine crystals is effected by applying an adhesive agent to the light-penetrating face of the test cell and causing the fine crystals to be fast deposited on the layer of the adhesive agent.

5. An apparatus for optical determination of the saturation temperature of a given substance dissolved in a solution under test comprising:
   a light source;
   a light receiving unit above said light source, and having a light receiving element and a first light path therein;
   a warmer positioned between said light source and said light receiving unit, said warmer having a second light path therethrough;
   a test cell supported by said warmer and extending through said second light path;
   an air seal glass supported by said warmer, said air seal glass being positioned above said test cell and extending through said second light path such that the distance between the test cell and the air seal glass is between 0.5 mm and several mm;
   said warmer being capable of warming said test cell;
   whereby light emitted from said light source passes through said second light path, said test cell, said air seal glass and said first light path, and is received by said light receiving element so as to optically determine the saturation temperature;
   the test cell, warmer and air seal glass forming a substantially closed space;
   air ducts pierced through said warmer and communicated with said closed space; and
   means to introduce a drying fluid to said closed space through said air ducts.

6. A device for the optical determination of a saturation temperature as in claim 5, wherein means are provided on the lower side of said light receiving unit to create an empty space between the lower portion of said light receiving unit and the upper portion of said warmer when said light receiving unit is mounted on said warmer during use.

* * * * *